United States Patent
Huatan et al.

(10) Patent No.: US 9,649,280 B2
(45) Date of Patent: *May 16, 2017

(54) COMPOSITION COMPRISING HYDROCORTISONE

(71) Applicant: Diurnal Limited, Cardiff (GB)

(72) Inventors: Hiep Huatan, Maidstone (GB); Richard Ross, Sheffield (GB); Martin Whitaker, Nottingham (GB); Norbert Poellinger, Mullheim (DE); Annette Grave, Lorrach (DE)

(73) Assignee: Diurnal Limited, Cardiff (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/888,648

(22) PCT Filed: May 12, 2014

(86) PCT No.: PCT/GB2014/051442
§ 371 (c)(1),
(2) Date: Nov. 2, 2015

(87) PCT Pub. No.: WO2014/184525
PCT Pub. Date: Nov. 20, 2014

(65) Prior Publication Data
US 2016/0081942 A1 Mar. 24, 2016

(30) Foreign Application Priority Data
May 17, 2013 (GB) .................................. 1308933.9

(51) Int. Cl.
*A61K 9/00* (2006.01)
*A61K 47/38* (2006.01)
*A61K 9/14* (2006.01)
*A61K 9/50* (2006.01)
*A61K 31/573* (2006.01)

(52) U.S. Cl.
CPC .......... *A61K 9/5078* (2013.01); *A61K 9/0053* (2013.01); *A61K 9/5015* (2013.01); *A61K 9/5042* (2013.01); *A61K 9/5047* (2013.01); *A61K 31/573* (2013.01)

(58) Field of Classification Search
CPC .............. A61K 2300/00; A61K 9/0053; A61K 9/2054; A61K 9/4808; A61K 9/14
See application file for complete search history.

(56) References Cited

U.S. PATENT DOCUMENTS

| 2005/0287211 | A1 | 12/2005 | Yoshida et al. |
| 2007/0281007 | A1* | 12/2007 | Jacob .................... A61K 9/006 424/452 |
| 2008/0187586 | A1 | 8/2008 | Skrtic et al. |
| 2009/0035375 | A1 | 2/2009 | Skrtic et al. |
| 2010/0029602 | A1* | 2/2010 | Arkin ................... A61K 9/0014 514/172 |
| 2014/0287052 | A1 | 9/2014 | Huatan et al. |

FOREIGN PATENT DOCUMENTS

| EP | 0 474 098 A1 | 3/1992 |
| WO | WO 97/25980 A1 | 7/1997 |
| WO | WO 2005/102271 A2 | 11/2005 |
| WO | WO 2005/102287 A2 | 11/2005 |
| WO | WO 2010/032006 A2 | 3/2010 |
| WO | WO 2010/115615 A1 | 10/2010 |
| WO | WO 2011/144327 A1 | 11/2011 |
| WO | WO 2013/072707 A1 | 5/2013 |
| WO | WO 2014/184525 A1 | 11/2014 |

OTHER PUBLICATIONS

Dauber et al., "Noctural Dexamethasone versus Hydrocortisone for the Treatment of children with Congenital Adrenal Hyperplasia," *Intl. J. Pediatric Endocrinol.* 2010:347636-347643, 2010.
Debono and Ross, "Doses and Steroids to be Used in Primary and Central Hypoadrenalism," *Ann. d'Endocrinol.* 68:265-267, 2007.
Möschwitzer and Müller, "Spray Coated Pellets as Carrier System for Mucoadhesive Drug Nanocrystals," *Eur. J. Pharm. Biopharm.* 62:282-287, 2006.
International Search Report and Written Opinion issued by European Patent Office on Jul. 24, 2014, for PCT/GB2014/051442, 10 pages.
Johannsson et al., "Improving Glucocorticoid Replacement Therapy Using a Novel Modified-Release Hydrocortisone Tablet: A Pharmacokinetic Study," *Eur. J. Endocrinol.* 161:119-130, 2009.
Lennernas et al., "Replacement Therapy of Oral Hydrocortisone in Adrenal Insufficiency: The Influence of Gastrointestinal Factors," *Expert Opin. Drug Metab. Toxicol.* 4:749-758, 2008.
Search Report under Section 17 issued by Intellectual Property Office on Mar. 2, 2012, for GB 1119985.8, 5 pages.
Search Report under Section 17(5) issued by Intellectual Property Office on Oct. 28, 2013, for GB1308933.9, 3 pages.

* cited by examiner

*Primary Examiner* — Frederick Krass
*Assistant Examiner* — Tracy Liu
(74) *Attorney, Agent, or Firm* — Klarquist Sparkman, LLP

(57) ABSTRACT

The disclosure relates to pharmaceutical compositions useful in the treatment of adrenal insufficiency in paediatric or elderly subjects.

23 Claims, 2 Drawing Sheets

COMPOSITION COMPRISING HYDROCORTISONE

CROSS REFERENCE TO RELATED APPLICATIONS

This is the U.S. National Stage of International Application No. PCT/GB2014/051442, filed May 12, 2014, which was published in English under PCT Article 21(2), which in turn claims the benefit of Great Britain Application No. 1308933.9, filed May 17, 2013.

FIELD OF THE INVENTION

The invention relates to pharmaceutical compositions comprising hydrocortisone and their use in the treatment of adrenal insufficiency in a paediatric or elderly subject.

BACKGROUND TO THE INVENTION

Adrenal failure occurs in approximately 1/10,000 of the adult population and 1/16,000 of infants. It may be due to either primary adrenal failure (e.g. Addison's disease commonly occurring following autoimmune damage to the adrenal gland) or tuberculosis; or secondary adrenal failure which occurs due to pituitary failure which may be caused by a pituitary tumour or surgery. In primary adrenal failure, ACTH levels from the pituitary will be high and in secondary adrenal failure ACTH levels are inappropriately low. Tertiary adrenal failure is another common cause of adrenal failure and leads to suppression of the normal pituitary-adrenal axis by steroid therapy such as that used in chemotherapy, rheumatoid arthritis and asthma. A further condition that results from adrenal failure is glucocorticoid-remediable aldosteronism (GRA) which results from increased secretion of aldosterone. Thus, adrenal failure is a relatively common condition and many patients have to take long-term steroid replacement therapy.

It is apparent that dosing regimens for the treatment of children, adults and elderly adults will vary depending on a number of parameters such as developmental stage and physiological state.

For example, the treatment of children suffering adrenal insufficiency is problematic for a number of reasons and treatment regimens used to treat adult subjects suffering adrenal failure are not equivalent when applied to non-adults [e.g. neonates, infants, small child, and pre-pubescent child]. The treatment of paediatric adrenal insufficiency has particular problems and requires pharmaceutical formulations that address the pharmacokinetic and pharmacodynamic problems of dosing infants. Hepatic microsomal enzyme processes are not fully developed in infants who may require alternative dosage and administration regimens of one, two or more doses of drug. In drugs that are cleared by the liver there is a gradual increase in drug clearance rate throughout childhood to the fully mature adult which once again requires careful monitoring of dose and dosage regimen.

Current preparations of hydrocortisone cannot adequately replace cortisol deficiency especially in the paediatric population because the formulations used do not allow the flexibility of (low) dose hydrocortisone to reproduce physiological levels of cortisol. For example, after diagnosis with adrenal insufficiency, usually at birth, a common dose of hydrocortisone prescribed in the United Kingdom is 7.5 mg per day divided into three equal doses (i.e. 3×2.5 mg per day). However, the smallest hydrocortisone tablet currently available in the United Kingdom and most of Europe is 10 mg hydrocortisone (5 mg hydrocortisone—Cortef® in the US). These tablets are often halved and/or quartered or crushed and repackaged to provide the required dose. Where a 10 mg hydrocortisone tablet is available, the 2.5 mg dose is usually the smallest dose attainable because it is difficult to accurately divide a tablet into more than four quarters. Where a 5 mg hydrocortisone tablet is available, a 1.25 mg dose is usually the smallest dose attainable.

In the United Kingdom, paediatric clinicians and patients believe that the 7.5 mg daily dose is far too high for neonates (0-28 days old), infants (1-24 months old) and young children (2-6 years old) and that the disease is not being adequately controlled but rather over treated. For example overtreatment with glucocorticoids such as hydrocortisone means that children suffer from very poor growth, poor weight-control and metabolic issues through development. One result of this glucocorticoid overtreatment in early childhood is that children never reached their full genetic height potential, suffer from low bone density at puberty (and into adulthood) and are at risk of obesity and a poor metabolic profile with increased cardiovascular risk factors in adult life.

For infants, crushed hydrocortisone tablets can give rise to dosing inconsistency as the poor solubility of the drug requires the use of suspension delivery methods which can lead to dose in homogeneity. Individual case reports have shown poor control of congenital adrenal hyperplasia with either excessive cortisol levels or low cortisol levels in association with poor androgen control after oral administration of crushed tablets. In addition infants and children do not like the taste of hydrocortisone making administration difficult and compliance unreliable. Studies investigating the bio-availability/pharmacokinetics on the stability of these tablets, when divided, have shown suboptimal treatment questioning the efficacy and ethics of such practice, particularly in the most vulnerable patients of all, neonates and infants.

Common problems in delivering hydrocortisone in accordance with levels required for normal and healthy growth in children are that: (a) currently available tablet formulations do not enable accurate, low dose titration of hydrocortisone, (b) such tablet formulations when crushed to facilitate suspension delivery suffer poor dose homogeneity and have only a limited shelf-life (less than 1 month at 4 degrees Centigrade) necessitating refrigerated storage and further complicating end use. Furthermore, if a subject receiving the medication is able to taste the active ingredient upon ingestion they may refuse to comply with the prescribed dosage regimen. This is particularly acute with paediatric and elderly patients who may have problems swallowing tablets or capsules. This is also a problem if multiple dosages are required throughout the day.

It is now increasingly recognised that all patients with adrenal insufficiency are receiving excess glucocorticoid because of the limited ability to dose titrate. This excess glucocorticoid is associated with an increased mortality rate in patients with adrenal insufficiency. In adults optimal treatment requires at least thrice daily dosing with a weight related dose. Total daily doses vary between 10 and 30 mg but as a larger dose is required in the morning current dosage formulations do not allow adequate titration putting patients at risk of either over or under treatment at different times of the day.

In our PCT application [WO2013/072707], we disclose hydrocortisone formulations that are substantially immediate release, are palatable and useful in the treatment of adrenal insufficiency in paediatric patients. The present disclosure relates to a further formulation not disclosed in WO2013/072707 and which has an improved properties. We also disclose regimens that show improved disease control in paediatric or elderly subjects, improved compliance and reduced side effect profile.

STATEMENTS OF INVENTION

According to an aspect of the invention there is provided a pharmaceutical composition adapted for oral administration comprising: a micro-particulate carrier comprising an effective amount of hydrocortisone and a binding agent and contacting said micro-particulate carrier a sealing polymer layer wherein the sealing polymer layer separates the microparticulate carrier and a taste masking polymer layer.

A paediatric subject includes neonates (0-28 days old), infants (1-24 months old), young children (2-6 years old) and prepubescent [7-14 years old]. An elderly subject includes those over about the age of 60 years old.

In a preferred embodiment of the invention an effective amount of hydrocortisone is between about 0.25 mg w/w and 30 mg w/w hydrocortisone per unit dose.

Preferably said effective amount is about 0.25 mg w/w, 0.5 mg w/w, 1.0 mg w/w, 2.0 mg w/w, 5.0 mg w/w, 10 mg w/w, 20 mg w/w or 30 mg w/w/per unit dose.

In a preferred embodiment of the invention said carrier comprises microcrystalline cellulose particles wherein the diameter of said particles is between 350-500 μm Preferably, the diameter of said particles is selected from the group consisting of: 350 μm, 375 μm, 400 μm, 425 μm, 450 μm, 475 μm or 500 μm.

Preferably the binding agent is between 0.60-0.70% w/w of the composition, preferably about 0.67% w/w.

In a preferred embodiment of the invention the binding agent is hydroxypropylmethylcellulose.

Preferably, the sealing layer comprises hydroxypropylmethylcellulose.

In a preferred embodiment of the invention the sealing layer is 15-25% w/w of the composition.

Preferably, said sealing layer is: 15% w/w, 16% w/w, 17% w/w, 18% w/w, 19% w/w, 20% w/w, 21% w/w, 22% w/w, 23% w/w, 24% w/w or 25% w/w of the composition.

Preferably, the sealing layer is about 20% w/w of the composition.

In a preferred embodiment of the invention said sealing layer comprises or consists essentially of about 18% w/w hydroxypropylmethylcellulose and about 2% magnesium stearate.

Taste masking or flavour enhancement of medication is known in the art and typically involves the use of molecules/polymers to mask the taste of the active or by disguising the taste by adding the medication to a flavoured food or drink. Examples of taste masking molecules can be selected from the Handbook of Excipients [2010] which are compatible with use in the paediatric population and represents common general knowledge. Alternatively or in addition masking the taste of the active could include the use of flavoured drinks or food, for example, combining the formulation with sugar favoured drink, e.g. fruit juice, flavoured water or cordial, semi-solid foods such as sauces, e.g. apple sauce, vegetable extracts e.g. Marmite®, dairy products such as yogurts, crème fraiche, cream. When administered to neonates, infants and young children the composition is administered by opening up the capsule and adding the composition directly into an aqueous or semi-aqueous vehicle as a suspension. The composition and vehicle combination can be administered by metered spoon (disposable/re-useable), via pre-filled spoon, via syringe, via dropper, via straw, or via dose-specific method.

In a preferred embodiment of the invention the taste masking polymer layer is a combination of hydroxypropylmethylcellulose and ethylcellulose.

In a preferred embodiment of the invention the taste masking polymer layer is provided between 0.5%-1.5% w/w of the composition. Preferably, the taste masking polymer layer is provided at about 1% w/w of the composition.

In a preferred embodiment of the invention hydroxypropylmethylcellulose is provided at about 0.2% w/w and ethylcellulose is provided at about 0.8% w/w of the composition.

In an alternative preferred embodiment of the invention the ratio of ethylcellulose to hydroxypropylmethylcellulose is 4:1 in the taste masking layer.

In a preferred embodiment of the invention said composition comprises:
  i) a carrier consisting essentially of at least 80-81% w/w micro-particulates wherein said micro-particulates are 350-500 μm in diameter;
  ii) a drug layer consisting essentially of at least 0.64-0.66% w/w hydrocortisone and at least 0.64-0.66% w/w hydroxypropylmethylcellulose contacting the carrier;
  iii) a sealing layer consisting essentially of at least 14-16% w/w hydroxypropylmethylcellulose and at least 1.0-2.0% w/w magnesium stearate contacting said drug layer; and
  iv) a taste masking layer consisting essentially of at least 0.14-0.16% w/w hydroxypropylmethylcellulose, at least 0.58-0.62% w/w ethylcellulose and at least 0.20-0.25% w/w magnesium stearate contacting said sealing layer.

Preferably, said composition comprises:
  i) a carrier consisting of 81% w/w micro-particulates;
  ii) a drug layer consisting of 0.66% w/w hydrocortisone and at 0.66% w/w hydroxypropylmethylcellulose contacting the carrier;
  iii) a sealing layer consisting of 15% w/w hydroxypropylmethylcellulose and 1.5% magnesium stearate contacting said drug layer; and
  iv) a taste masking layer consisting of 0.15% w/w hydroxypropylmethylcellulose, at least 0.61% w/w ethylcellulose and at least 0.23% w/w magnesium stearate contacting said sealing layer.

In a preferred embodiment of the invention composition is adapted for substantially immediate release of hydrocortisone.

Preferably, hydrocortisone is not substantially released before about 5 minutes in aqueous conditions in the mouth.

In a preferred embodiment of the invention hydrocortisone is released after swallowing.

According to a further aspect of the invention there is provided a composition according to the invention for use in the treatment of adrenal insufficiency.

Preferably the adrenal insufficiency is caused by a condition selected from the group consisting of: primary or secondary or tertiary adrenal failure, congenital adrenal hyperplasia, late-onset congenital adrenal hyperplasia, polycystic ovarian failure, Glucocorticoid-remediable aldosteronism (GRA).

In a preferred embodiment of the invention adrenal insufficiency is caused by congenital adrenal dysfunction.

Compositions suitable for oral administration may be presented as discrete units, such as capsules, tablets, mini-tablets, lozenges, each containing a predetermined amount of the active.

In a preferred embodiment of the invention said composition is a tablet or capsule; preferably a capsule.

Other compositions include suspensions in aqueous liquids or non-aqueous liquids. Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

When administered the hydrocortisone preparation is administered in pharmaceutically acceptable preparations. Such preparations may routinely contain pharmaceutically acceptable concentrations of salt, buffering agents, preservatives and compatible carriers.

Such amounts will depend, of course, on the particular condition being treated, the severity of the condition, the individual patient parameters including age, physical condition, size and weight, the duration of the treatment, the nature of concurrent therapy (if any), and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

The hydrocortisone preparation used contains an effective amount of drug for producing the desired response in a unit of weight or volume suitable for administration to a patient.

The doses of hydrocortisone administered to a subject can be chosen in accordance with different parameters, in particular the state of the subject, their body surface area, and also their weight. Other factors include the desired period of treatment. In the event that a response in a subject is insufficient at the initial doses applied, higher doses (or effectively higher doses by a different, more localized delivery route) may be employed to the extent that patient tolerance permits.

Administration of hydrocortisone preparations to mammals other than humans, (e.g. for testing purposes or veterinary therapeutic purposes), is carried out under substantially the same conditions as described above although dosages will vary in accordance with the size of the animal treated. Steroid treatment is used in animals both for any cause of adrenal insufficiency but in addition for any cause of inflammation, joint disease, and cancer. A subject, as used herein, is a mammal, preferably a human, and including a non-human primate, cow, horse, pig, sheep, goat, dog, cat or rodent.

When administered, the hydrocortisone preparation is administered in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Hydrocortisone preparations may be combined, if desired, with a pharmaceutically-acceptable carrier. The term "pharmaceutically-acceptable carrier" as used herein means one or more compatible solid or liquid fillers, diluents or encapsulating substances which are suitable for administration into a human and are typically inert. The term "carrier" denotes an organic or inorganic ingredient, natural or synthetic, with which the active ingredient is combined to facilitate the application. The components of the pharmaceutical compositions also are capable of being co-mingled with hydrocortisone, and with each other, in a manner such that there is no interaction which would substantially impair the desired pharmaceutical efficacy.

The multiparticulate core matrix is combined with pharmaceutically acceptable excipients, which may include: (a) fillers such as lactose, manitose, dicalcium phosphate, microcrystalline cellulose, starch, pre-gelatanised starch, (b) binders such as hydroxypropylmethyl cellulose, polyvinyl pyrrolidone, polyvinyl acetate, (c) powder flow enhancers such colloidal silicon dioxide (d) lubricants such as magnesium stearate, sodium stearyl fumarate (e) disintegrants such as sodium starch glycollate and polyvinyl pyrrolidone and (f) anti-sticking agents such as talc (g) taste masking agents such as sucrose, cellulose acetate, cellulose butyrate, polyvinyl acetate, polyvinyl alcohol, polymetharylates.

According to a further aspect of the invention there is provided a treatment regimen for the control of adrenal insufficiency in a paediatric subject comprising: administering an effective amount of a composition according to the invention to a subject in need of treatment for adrenal insufficiency at least once a day.

In a preferred method of the invention said composition is administered three to four times a day at approximately six hour intervals.

DEFINITIONS

"Binding agent": is a substance used to cause adhesion of powder particles in tablet granulations such as: Alginic acid, carboxymethylcellulose, sodium compressible sugar, ethylcellulose gelatin, liquid glucose, methylcellulose, povidone, pregelatinized starch.

"Micro-particulate carrier": is defined as a particulate dispersions or solid particles with a size in the range of 1-1000 μm on which the desired drug is dissolved, entrapped, encapsulated or attached to a microparticle matrix.

"Sealing polymer coat": provides a moisture barrier and a hard tablet surface to prevent attritional effects. Coating materials include sugar, waxes, shellac, cellulose derivatives, gelatin, organic acids, aminoalkyl aryl polymers or polyvinylstyrene compounds.

"Immediate release": a dosage form that is intended to release the active ingredient(s) on administration or after a short delay with no enhanced, delayed or extended release effect.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF SUMMARY OF THE DRAWINGS

An embodiment of the invention will now be described by example only and with reference to the following figure, materials and methods.

MATERIALS AND METHODS

Dissolution Methodology

Figure 1:
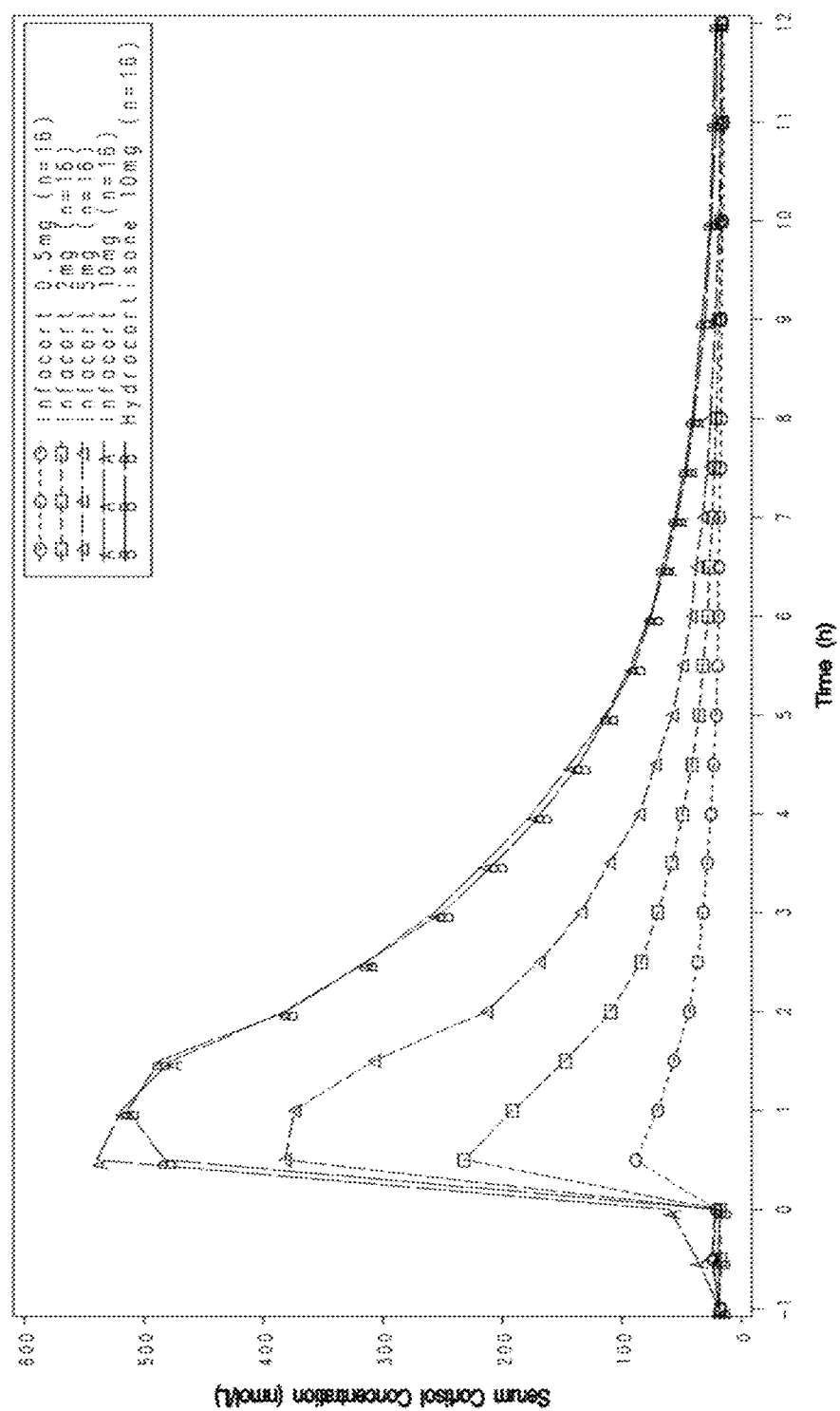
FIG. 1 illustrates the dose proportionality of hydrocortisone administered to dexamethasone suppressed adult subjects.

Dissolution testing of Hydrocortisone Immediate Release multi-particulates was conducted using USP Apparatus II (Paddles), with a total of 900 mL of dissolution media, involving two subsequent sequential media changes, and a paddle speed of 75 rpm. Dissolution was conducted initially in 700 mL of simulated gastric fluid (USP, pH 1.2) for 2 hours Assay of Hydrocortisone The concentration of hydrocortisone in the multi-particulates and released during the dissolution evaluation was determined using the following method. The hydrocortisone solution was diluted in the mobile phase solution comprising tetrahydrofuran/water (20:80 v/v). The resulting solution was into a HPLC, set-up with a Phenomenex Luna column C18(2), 5 μm, 150 mm×4.6 mm, equilibrated at 45° C. The samples were run using Isocratic conditions employing tetrahydrofuran/water (20:80 v/v) as the mobile phase at a flow rate of 1.5 mL/minute. Detection is by UV at a wavelength of 254 nm.

Dosage Regimen for Paediatric Patients

In infants hydrocortisone is usually administered in a dose of 12 to 18 mg/m2 body surface area per day. In the early phase of treatment, infants may require up to 25 mg/m2/day of hydrocortisone to reduce markedly elevated adrenal hormones. This dose range exceeds the daily cortisol secretory rate of normal infants and children, which is estimated to be 7 to 9 mg/m2 body surface area in neonates and 6 to 7 mg/m2 body surface area in children and adolescents. The treatment is usually split into three or four doses. In a premature infant you might use 0.25 mg four times daily given six hourly. In a normal sized neonate you would be looking at 0.5 mg to 1.0 mg thrice or four times daily (6 hourly). For infants and children up to six years of age dosing would be between 1.0 to 2.0 mg three times daily with the first dose given on waking the second at midday and the third in the evening; a larger dose usually being given in the morning. The same is true for adolescents but the total daily dose would be increased according to body surface area to between 5 to 20 mg. In the dosing regimen would be best given thrice daily as illustrated in table 1.

| Patient Weight (kg) | Total Hydro-cortisone Dose per day (mg) | First Morning Hydro-cortisone Dose (mg) | Second Midday Hydro-cortisone Dose (mg) | Third Evening Hydro-cortisone Dose (mg) |
|---|---|---|---|---|
| 50-54 | 10.0 | 5.0 | 2.5 | 2.5 |
| 55-74 | 15.0 | 7.5 | 5.0 | 2.5 |
| 75-84 | 17.5 | 10.0 | 7.5 | 2.5 |
| 85-94 | 20.0 | 10.0 | 7.5 | 2.5 |
| 95-114 | 22.5 | 12.5 | 7.5 | 2.5 |
| 115-120 | 25.0 | 15.0 | 7.5 | 2.5 |

TABLE 2

| Components | | % |
|---|---|---|
| 0795/2012 (drug layer) | Cellets 350 | 81.18 |
|  | Hydrocortisone Micro. | 0.66 |
|  | Pharmacoat 603 | 0.66 |
| 0804/2012 (seal coat) | Pharmacoat 606 | 15.00 |
|  | Mg-stearate | 1.50 |
| 0044/2013 (taste mask) | Pharmacoat 603 | 0.15 |
|  | Ethocel standard 10 | 0.61 |
|  | Mg -Stearate | 0.23 |

TABLE 3

| Batch/time (minutes) | 0084; 0.5 mg; 20% SC, EC/HPMC: 80/20 - 1% coating level | 0085; 5 mg; 20% SC, EC/HPMC: 80/20 - 1% coating level |
|---|---|---|
| 0 | 0.00 | 0.00 |
| 15 | 79.64 | 77.52 |
| 30 | 87.88 | 86.71 |
| 45 | 90.74 | 90.62 |
| 60 | 92.22 | 92.13 |
| 120 | 92.08 | 94.44 |

Dosage Regimen in Adult Subjects

To study cortisol levels in healthy adult subjects it was necessary to suppress endogenous cortisol levels using the synthetic glucocorticoid dexamethasone. Dexamethasone reduces ACTH release from the pituitary gland therefore leading to suppressed cortisol output from the adrenals. ACTH samples were collected prior to IMP dosing to confirm ACTH output had been suppressed. Since the administration of dexamethasone took place over a single 14 hr period in each of 5 treatment periods (separated by at least 7 days), it was considered that this non-continuous regimen would not lead to a risk of adrenal suppression and the total dose of dexamethasone was less than that used in clinical practice in tests of cortisol secretion.

A washout period of a minimum of 7 days was considered adequate based on the half-life ($t_{1/2}$) of hydrocortisone being ~100 minutes. This washout period was also considered sufficient to allow hormone levels to return to normal.

Each investigational medicinal product (IMP) was administered to each subject in a randomised crossover manner. Each subject received their scheduled IMP on the morning of Day 2 at ~07.00 hrs (fasted). Treatments were administered as displayed in Table 4.

TABLE 4

Treatments administered

| N | IMP | | |
|---|---|---|---|
| 16 | hydrocortisone immediate release | 0.5 mg | Multi-particulate granules from 1 (0.5 mg) capsule |
| | hydrocortisone immediate release | 2 mg | Multi-particulate granules from 1 (2 mg) capsule |
| | hydrocortisone immediate release | 5 mg | Multi-particulate granules from 1 (5 mg) capsule |
| | hydrocortisone immediate release | 10 mg | Multi-particulate granules from 2 (5 mg) capsules |
| | Hydrocortisone | 10 mg | 1 (10 mg) tablet |

The hydrocortisone immediate release capsules were opened, the entire contents (multi-particulate granules) emptied onto a dosing spoon, administered to the back of the subject's tongue and swallowed with 200 mL water (100 mL to swallow the treatment and 100 mL rinse). The hydrocortisone tablets were swallowed whole with 200 mL water. Each subject also received 1 mg dexamethasone (to suppress endogenous cortisol production) at approximately 22.00 hrs on Day 1, and at approximately 06.00 hrs and 12.00 hrs on Day 2. All doses were administered with 200 mL water.

Selection of Doses in the Study

Hydrocortisone immediate release is a newly-developed formulation of immediate release hydrocortisone for use in the paediatric population. The formulation chosen is a dry hydrocortisone multi-particulate formulation stored in capsules where the capsule contents (the multi-particulates) may be administered either directly into the patient's mouth or placed on a (dry) spoon and then administered into the patient's mouth.

The advantages of this formulation strategy are:
Multi-particulates offer flexible dosing in 0.5 mg, 1 mg, 2 mg and 5 mg strengths.
Multi-particulates will be presented as different-coloured capsules for different doses, thus minimizing the risk of dosing errors.
Accurate, complete dosing—the patient will receive the full dose required.
Multi-particulates will have a water soluble layer allowing taste masking and rapid dissolution once ingested.
Long-term stability (potentially months/years).
No compatibility issues with liquid vehicles.

Four dosing units are envisaged: 0.5 mg, 1 mg, 2 mg and 5 mg. This range has been chosen as being suitable to cover the dosing needs of children from birth to <6 years. hydrocortisone immediate release was studied in healthy adult subjects, to enable the relative bioavailability and key PK parameters of the new formulation to be assessed, prior to evaluation in the paediatric population.

A 10 mg dose of hydrocortisone immediate release was used to compare the PK of this new formulation with that of the marketed immediate-release 10 mg hydrocortisone tablet. Hydrocortisone at a dose of 10 mg is a standard dose used in the clinical setting. To study cortisol levels in healthy adult subjects it was necessary to suppress endogenous cortisol levels using the marketed synthetic glucocorticoid dexamethasone. Dexamethasone at a dose of 1 mg is the lower end of the standard dosage used in the clinical setting.

Timing of Dose for Each Subject

Doses of IMP were administered at approximately 07:00 hrs on Day 2 during each treatment period (taking dosing intervals between subjects into account).

Dexamethasone 1 mg was administered orally at ~22:00 hrs on Day 1 and at ~06:00 hrs and ~12:00 hrs on Day 2

Subjects were required to fast from ~19:00 hrs on Day 1 until 08:00 hrs on Day 2 of each treatment period.

Serum Cortisol Measurement

PK blood sampling was performed during the study were collected on Day 2 pre-dose (−1 hr and −0.5 hr) and 0 hr (07.00 hrs), 0.5, 1, 1.5, 2, 2.5, 3, 3.5, 4, 4.5, 5, 5.5, 6, 6.5, 7, 7.5, 8, 9, 10, 11 and 12 hr post-dose.

Blood samples (2.7 mL) for determination of serum cortisol levels were collected from a forearm vein into plain blood collection tubes at each time point, and kept frozen at approximately −20° C. pending analysis. Samples were analysed using a validated method, the specificity of which was checked against co-administered dexamethasone.

The following PK End-points were determined: Maximum plasma concentration (Cmax); time at which Cmax occurs (tmax); area under the concentration-time curve (AUC) to the time of last observed concentration (AUC0-t) and extrapolated to infinity (AUC0-inf).

Plasma ACTH

Blood samples (2.7 mL) for determination of plasma ACTH levels were collected from a forearm vein into iced Sarstedt K3 ethylene-diamine-tetraacetic acid (EDTA) Monovette® at each time point and kept frozen at −20° C. until analysis. Blood samples were analysed within 30 days of the sample being taken, using a validated method. Blood samples for measurement of ACTH levels were collected on Day 2 at 0 hr (~07.00 hrs).

Statistical Methods:

Mean serum cortisol concentration-time curves were adjusted to exclude individual treatment profiles from subjects where the pre-dose cortisol demonstrates inadequate suppression.

EXAMPLE 1

In order to determine whether hydrocortisone immediate release is bioequivalent with Hydrocortisone equivalent doses of 10 mg were given to subjects as described in Materials and Methods. As shown in Table 5, 10 mg hydrocortisone immediate release was considered bioequivalent to the reference hydrocortisone formulation. The $t_{max}$ and t½ were also similar between 10 mg hydrocortisone immediate release and the reference hydrocortisone, with a median $t_{max}$ of 0.75 hrs and 1.0 hr respectively (p=0.4772) at similar halftimes ($t_{1/2}$ of 1.34 hrs and 1.31 hrs, respectively) indicating no differences in rate of absorption and $t_{1/2}$.

TABLE 5

Summary of Statistical Analysis of Bioequivalence
Between 10 mg hydrocortisone immediate release ® and
10 mg Hydrocortisone using Adjusted Data

|  | hydrocortisone immediate release 10 mg (n = 14) | Hydrocortisone 10 mg (n = 14) | hydrocortisone immediate release 10 mg vs. Hydrocortisone 10 mg |
|---|---|---|---|
| $C_{max}$ (nmol/L) | 565.97 | 597.59 | 94.71 (83.51-107.40) |
| $AUC_{0-t}$ (hr*nmol/L) | 1595.91 | 1575.82 | 101.27 (95.78-107.09) |
| $AUC_{0-inf}$ (hr*nmol/L) | 1601.89 | 1585.48 | 101.03 (95.45-106.94) |

|  | Median | Median Difference (95% C.I.) (p-value[a]) |
|---|---|---|
| $t_{max}$ (hr) | 0.75    1.00 | 0.00 (−0.50-0.25) (0.4772) |

Results obtained using a mixed effects ANOVA with fixed effects of study period, sequence and treatment and a random effect of subject (sequence) (excl. $t_{max}$). $t_{max}$ results obtained using the method of Campbell and Gardner and the [a] Wilcoxon Matched Pairs test.

EXAMPLE 2

Dose proportionality of hydrocortisone immediate release was tested by administering different concentrations of hydrocortisone immediate release and determining PK values and ACTH serum levels. As shown in Table 6 and illustrated graphically in FIG. 1, when the four doses of hydrocortisone immediate release were tested for dose-proportionality, over the 0.5 mg-10 mg dose range $C_{max}$, $AUC_{0-t}$ and $AUC_{0-inf}$ were shown to increase in a linear fashion (Table 1, FIG. 1). Similarly, ACTH serum levels decrease over time on a linear scale.

TABLE 3

PK values for hydrocortisone immediate release given at different concentrations

|  | hydrocortisone immediate release 0.5 mg (n = 15) | hydrocortisone immediate release 2 mg (n = 15) | hydrocortisone immediate release 5 mg (n = 15) | hydrocortisone immediate release 10 mg (n = 14) | Slope | 95% C.I. for Slope |
|---|---|---|---|---|---|---|
|  | Dose Proportionality |  |  |  |  |  |
| $C_{max}$ (nmol/L) | 90.09 | 243.02 | 418.31 | 599.30 | 0.637 | 0.600-0.675 |
| $AUC_{0-t}$ (hr * nmol/L) | 316.97 | 639.81 | 1111.03 | 1776.70 | 0.571 | 0.552-0.590 |
| $AUC_{0-inf}$ (hr * nmol/L) | 505.71 | 785.45 | 1213.24 | 1871.21 | 0.428 | 0.392-0.464 |

Results for $C_{max}$ and AUCs obtained using an ANOVA on log-transformed data with a fixed effect of log-transformed dose and a random effect of subject.

EXAMPLE 3

Figure 2:
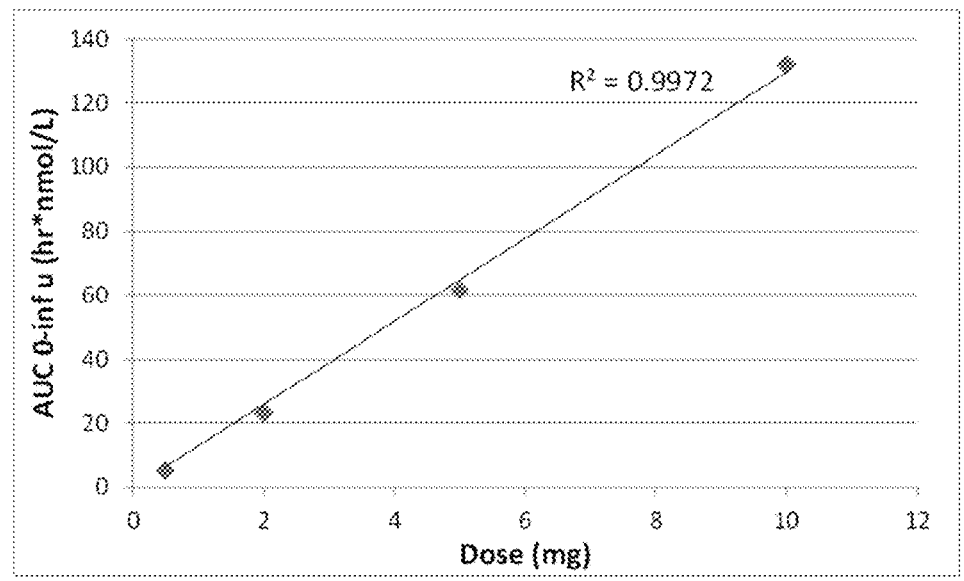
FIG. 2 demonstrates that the dose is directly proportional to the area under the plasma concentration. $R^2=0.9972$.
Figure 3:
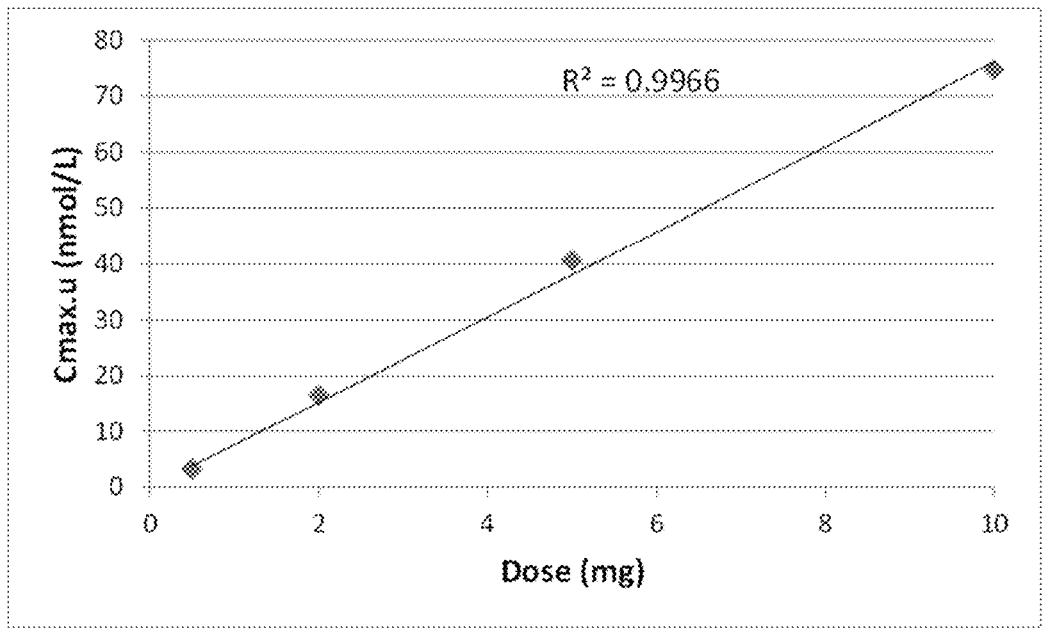
FIG. 3 demonstrates that the dose is directly proportional to $C_{max}$. $R^2=0.9966$.

In order to determine pharmacokinetic parameters such as clearance or bioavailability the area under the plasma concentration time curve (AUC) and $C_{max}$ was determined over time. As shown in FIGS. 2 and 3 AUC and $C_{max}$ respectively are directly proportional to the dose ($R^2$=0.9972 and $R^2$=0.9966) after values were adjusted for protein binding.

The hydrocortisone immediate release micro-particulate granules were safe, well tolerated and of neutral taste when administered to human volunteers.

The invention claimed is:

1. A pharmaceutical composition adapted for oral administration comprising:
   a micro-particulate carrier;
   a drug layer comprising an effective amount of hydrocortisone and a binding agent;
   a taste masking polymer layer comprising 0.14-0.16% w/w hydroxypropylmethylcellulose and 0.58-0.62% w/w ethylcellulose; and
   a sealing polymer layer that separates the drug layer and the taste masking polymer layer, wherein the sealing polymer layer consists of 14-16% w/w hydroxypropylmethylcellulose and 1-2% w/w magnesium stearate;
   wherein the drug layer is in contact with the micro-particulate carrier and with the sealing polymer layer.

2. The composition according to claim 1 wherein said effective amount of hydrocortisone is between about 0.25 mg w/w and 30 mg w/w hydrocortisone per unit dose.

3. The composition according to claim 1, wherein said carrier comprises microcrystalline cellulose particles with a diameter of between 350-500 μm.

4. The composition of claim 1, wherein the binding agent is between 0.60-0.70% w/w of the composition.

5. The composition according to claim 1, wherein the binding agent is hydroxypropylmethylcellulose.

6. The composition according to claim 1, wherein the sealing layer is 15-25% w/w of the composition.

7. The composition according to claim 1, wherein said sealing layer consists of about 15% w/w hydroxypropylmethylcellulose and about 1.5% w/w magnesium stearate.

8. The composition according to claim 1, wherein the taste masking polymer layer is between 0.5%-1.5% w/w of the composition.

9. The composition according to claim 1, wherein the taste masking polymer layer comprises hydroxypropylmethylcellulose is at about 0.15% w/w of the composition and ethylcellulose at about 0.60% w/w of the composition.

10. The composition according to claim 1, wherein the weight ratio of ethylcellulose to hydroxypropylmethylcellulose is 4:1 in the taste masking layer.

11. The pharmaceutical composition of claim 1, wherein:
   i) the micro-particulate carrier comprises 80-81% w/w micro-particulates, wherein said micro-particulates are 350-500 μm in diameter;

ii) the drug layer comprises 0.64-0.66% w/w hydrocortisone and 0.64-0.66% w/w hydroxypropylmethylcellulose;

iii) the sealing layer consists of 14-16% w/w hydroxypropylmethylcellulose and 1.0-2.0% w/w magnesium stearate; and iv) the taste masking layer further comprises 0.20-0.25% w/w magnesium stearate.

12. The pharmaceutical composition according to claim 11 wherein:

i) the micro-particulate carrier consists of 81% w/w micro-particulates;

ii) the drug layer consists of 0.66% w/w hydrocortisone and 0.66% w/w hydroxypropylmethylcellulose;

iii) the sealing layer consists of 15% w/w hydroxypropylmethylcellulose and 1.5% magnesium stearate; and iv) the taste masking layer consists of 0.15% w/w hydroxypropylmethylcellulose, 0.61% w/w ethylcellulose, and 0.23% w/w magnesium stearate.

13. The composition according to claim 1, wherein the composition is adapted for immediate release of hydrocortisone.

14. The composition according to claim 13 wherein hydrocortisone is not released before about 5 minutes in aqueous conditions in the mouth.

15. The composition according to claim 13 wherein hydrocortisone is released after swallowing.

16. The composition according to claim 15, wherein:

at least 70% of hydrocortisone contained in said composition is released 15 minutes after swallowing, or at least 90% of hydrocortisone contained in said composition is released 60 minutes after swallowing.

17. A method of treating adrenal insufficiency in a subject, comprising:

administering an effective amount of the composition of claim 1 to the subject, thereby treating the adrenal insufficiency.

18. The method according to claim 17, wherein the adrenal insufficiency is caused by primary or secondary or tertiary adrenal failure, congenital adrenal hyperplasia, late-onset congenital adrenal hyperplasia, polycystic ovarian failure, or glucocorticoid-remediable aldosteronism (GRA).

19. The method of claim 17, wherein the subject is a paediatric subject, and wherein the composition is administered at least once a day.

20. The method according to claim 19, wherein said composition is administered three to four times a day at approximately six hour intervals.

21. A pharmaceutical composition adapted for oral administration, comprising:

i) a carrier comprising 80-81% w/w micro-particulates, wherein said micro-particulates are 350-500 μm in diameter;

ii) a drug layer comprising 0.64-0.66% w/w hydrocortisone and 0.64-0.66% w/w hydroxypropylmethylcellulose, in contact with the carrier;

iii) a sealing layer consisting of 14-16% w/w hydroxypropylmethylcellulose and 1.0-2.0% w/w magnesium stearate, in contact with the drug layer; and iv) a taste masking layer comprising 0.14-0.16% w/w hydroxypropylmethylcellulose, 0.58-0.62% w/w ethylcellulose, and 0.20-0.25% w/w magnesium stearate, in contact with the sealing layer.

22. A pharmaceutical composition adapted for oral administration, comprising:

i) a carrier consisting of 81% w/w micro-particulates;

ii) a drug layer consisting of 0.66% w/w hydrocortisone and 0.66% w/w hydroxypropylmethylcellulose, in contact with the carrier;

iii) a sealing layer consisting of 15% w/w hydroxypropylmethylcellulose and 1.5% magnesium stearate, in contact with the drug layer; and iv) a taste masking layer consisting of 0.15% w/w hydroxypropylmethylcellulose, 0.61% w/w ethylcellulose, and 0.23% w/w magnesium stearate, in contact with the sealing layer.

23. A pharmaceutical composition adapted for oral administration comprising:

a micro-particulate carrier;

a drug layer comprising an effective amount of hydrocortisone and a binding agent;

a taste masking layer comprising 0.14-0.16% w/w hydroxypropylmethylcellulose and 0.58-0.62% w/w ethylcellulose; and a sealing polymer layer that separates the drug layer and the taste masking polymer layer wherein the sealing polymer layer consists of 15% w/w hydroxypropylmethylcellulose and 1.5% w/w magnesium stearate;

wherein the drug layer is in contact with the micro-particulate carrier and with the sealing polymer layer.

* * * * *